United States Patent
Zhang et al.

(10) Patent No.: US 9,352,304 B2
(45) Date of Patent: May 31, 2016

(54) METHODS FOR PREPARING ETHYLENE GLYCOL FROM POLYHYDROXY COMPOUNDS

(75) Inventors: Tao Zhang, Dalian (CN); Zhijun Tai, Dalian (CN); Aiqin Wang, Dalian (CN); Mingyuan Zheng, Dalian (CN)

(73) Assignee: DALIAN INSTITUTE OF CHEMICAL PHYSICS, CHINESE ACADEMY OF SCIENCES, Dalian, Liaoning (CN)

( * ) Notice: Subject to any disclaimer, the term of this patent is extended or adjusted under 35 U.S.C. 154(b) by 664 days.

(21) Appl. No.: 13/395,470

(22) PCT Filed: Nov. 4, 2010

(86) PCT No.: PCT/CN2010/078413
§ 371 (c)(1),
(2), (4) Date: Mar. 12, 2012

(87) PCT Pub. No.: WO2011/113281
PCT Pub. Date: Sep. 22, 2011

(65) Prior Publication Data
US 2012/0172633 A1 Jul. 5, 2012

(30) Foreign Application Priority Data
Mar. 17, 2010 (CN) .......................... 2010 1 0125806

(51) Int. Cl.
C07C 29/00 (2006.01)
B01J 23/888 (2006.01)
B01J 23/652 (2006.01)
C07C 29/132 (2006.01)
B01J 23/30 (2006.01)
B01J 23/42 (2006.01)
B01J 23/46 (2006.01)
B01J 23/755 (2006.01)
B01J 35/00 (2006.01)

(52) U.S. Cl.
CPC ............ B01J 23/888 (2013.01); B01J 23/6527 (2013.01); C07C 29/132 (2013.01); B01J 23/30 (2013.01); B01J 23/42 (2013.01); B01J 23/462 (2013.01); B01J 23/468 (2013.01); B01J 23/755 (2013.01); B01J 35/0006 (2013.01)

(58) Field of Classification Search
CPC ...................................................... C07C 27/00
USPC ........................................................ 568/861
See application file for complete search history.

(56) References Cited

U.S. PATENT DOCUMENTS

| | | | |
|---|---|---|---|
| 3,684,579 A | 8/1972 | Mund et al. | |
| 4,155,928 A | 5/1979 | Finch | |
| 6,297,185 B1 | 10/2001 | Thompson et al. | |
| 7,767,867 B2 | 8/2010 | Cortright | |
| 7,960,594 B2 * | 6/2011 | Zhang et al. | 568/861 |
| 8,222,462 B2 | 7/2012 | Kalnes et al. | |
| 8,222,463 B2 | 7/2012 | Kalnes et al. | |
| 8,222,464 B2 | 7/2012 | Kalnes et al. | |
| 8,222,465 B2 | 7/2012 | Kalnes et al. | |
| 8,323,937 B2 * | 12/2012 | Zhang et al. | 435/158 |
| 8,324,433 B2 | 12/2012 | Zhang et al. | |
| 8,338,326 B2 | 12/2012 | Zhang | |
| 2002/0198101 A1 | 12/2002 | Gaffney | |
| 2007/0269707 A1 | 11/2007 | Lee et al. | |
| 2009/0177018 A1 * | 7/2009 | Suzuki et al. | 568/861 |
| 2010/0256424 A1 * | 10/2010 | Zhang et al. | 568/861 |
| 2011/0312051 A1 | 12/2011 | Kalnes et al. | |
| 2011/0312487 A1 | 12/2011 | Chen et al. | |

FOREIGN PATENT DOCUMENTS

| | | |
|---|---|---|
| CN | 101117222 A | 2/2008 |
| CN | 101411975 A | 4/2009 |
| CN | 101428213 A | 5/2009 |

(Continued)

OTHER PUBLICATIONS

Na Ji, et al. "Catalytic Conversion of Cellulose into Ethylene Glycol Over Supported Carbide Catalysts." Catalysis Today, vol. 147 (2009), pp. 77-85.

Primary Examiner — Yong Chu
Assistant Examiner — Sonya Wright
(74) Attorney, Agent, or Firm — Novick, Kim & Lee, PLLC; Allen Xue

(57) ABSTRACT

This invention provides methods for producing ethylene glycol from polyhydroxy compounds such as cellulose, starch, hemicellulose, glucose, sucrose, fructose, fructan, xylose and soluble xylooligosaccharides. The methods uses polyhydroxy compounds as the reactant, a composite catalyst having active components comprising one or more transition metals of Groups 8, 9, or 10, including iron, cobalt, nickel, ruthenium, rhodium, palladium, iridium, and platinum, as well as tungsten oxide, tungsten sulfide, tungsten hydroxide, tungsten chloride, tungsten bronze oxide, tungsten acid, tungstate, metatungstate acid, metatungstate, paratungstate acid, paratungstate, peroxotungstic acid, pertungstate, heteropoly acid containing tungsten. Reacting at a temperature of 120-300° C. and a hydrogen pressure of 1-13 MPa under hydrothermal conditions to accomplish one-step catalytic conversion. It realizes efficient, highly selective, high yield preparation of ethylene glycol and propylene glycol from polyhydroxy compounds. The advantage of processes disclosed in this invention include renewable raw material and high atom economy. At the same time, compared with other technologies that converts biomass raw materials into polyols, methods disclosed herein enjoy advantages including simple reaction process, high yield of targeted products, as well as easy preparation and low cost for the catalysts.

21 Claims, No Drawings

(56) References Cited

FOREIGN PATENT DOCUMENTS

| | | |
|---|---|---|
| CN | 101648140 A | 2/2010 |
| CN | 101869853 A | 10/2010 |
| CN | 102049273 A | 5/2011 |
| WO | 02/28544 A1 | 4/2002 |
| WO | 2010017681 A1 | 2/2010 |

\* cited by examiner

METHODS FOR PREPARING ETHYLENE GLYCOL FROM POLYHYDROXY COMPOUNDS

TECHNOLOGY FIELD

The invention relates to methods for producing ethylene glycol, and more particularly to methods for producing ethylene glycol by catalytic hydrogenation to degrade polyhydroxy compounds under hydrothermal conditions.

DESCRIPTION OF THE RELATED ART

Ethylene glycol is an important liquid fuel and is also a very important raw material for making polyester, e.g., polyethylene terephthalate (PET), polyethylene naphthalate (PEN). It can also be used as antifreeze, lubricant, plasticizer, surfactant, etc. It is a widely used raw material for organic chemical industry.

Conventional methods for producing ethylene glycol involve petroleum as the raw material. For example, ethylene is epoxidized to yield ethylene oxide which is hydrated to yield ethylene glycol, [Literature 1: CUI Xiao-ming, the overview of the production development of ethylene glycol, Chemical Industry, 2007, 25, (4), 15-21, Literature 2: Process for preparing ethanediol by catalyzing epoxyethane hydration, Patent No. CN1463960-A; CN1204103-C]. These methods rely on oil—a non-renewable resource—and include a step of selective oxidization or epoxidation, which increases the technical difficulty of the process. Furthermore, conventional methods have low efficiency and high material consumption, can produce serious pollution, and produce a large quantity of by-products.

Producing ethylene glycol from renewable raw materials can reduce human dependence on fossil energy resources and contribute to sustainable development in terms of both the environment and the economy.

Polyhydroxy compounds, such as cellulose, starch, hemicellulose, glucose, sucrose, fructose, fructan, xylose and soluble xylooligosaccharides are very common in nature and the productions thereof are on the rise with the development of agricultural technologies. Making ethylene glycol using polyhydroxy compounds not only reduces human dependence on fossil energy resources but also produces value-added chemicals from agricultural products.

Current methods for producing ethylene glycol from polyhydroxy compounds [Literature 3: Process for the preparation of lower polyhydric alcohols, U.S. Pat. No. 5,107,018, Literature 4: Preparation of lower polyhydric alcohols, U.S. Pat. No. 5,210,335, Literature 5: A new method for ethylene glycol preparation, CN200610068869.5, and Literature 6: A method for preparation of diol and polyols via sorbitol hydrogenolysis, CN200510008652.0] usually includes three steps: (a) gelatinizing, liquefying, and saccharifying of polyhydroxy compounds to yield glucose; (b) hydrogenating the glucose with ruthenium or nickel as catalyst to yield sorbitol; and (c) degrading the sorbitol by hydrogenolysis under high temperature and high pressure conditions to yield a mixture that mainly includes propylene glycol, glycerol, and ethylene glycol. The yield of ethylene glycol is between 10% and 30%. The process is complex.

Another method for ethylene glycol preparation is through hydrogenolysis of cellulose under hydrothermal conditions [Literature 7: Direct catalytic conversion of cellulose into ethylene glycol using nickel-promoted tungsten carbide catalysts, Angew. Chem. Int. Ed. 2008, 47, 8510-8513, and Literature 8: transition metal—tungsten bimetallic catalysts for the conversion of cellulose into ethylene glycol, ChemSusChem 2010, 3, 63-66.] Tungsten carbide or metallic tungsten promoted by metallic transition metals was employed as catalysts for cellulose conversion, giving ethylene glycol yields in range of 60-75%.

The invention provides methods for producing ethylene glycol directly from polyhydroxy compounds using composite catalysts. Not only the reaction process is simple and the yield of ethylene glycol is high but also the catalyst is simple and easy prepare with low cost.

SUMMARY OF THE INVENTION

The invention provides methods for producing ethylene glycol from polyhydroxy compounds. Polyhydroxy compounds, including but not limited to cellulose, starch, hemicellulose, glucose, sucrose, fructose, fructan, xylose and soluble xylooligosaccharides, are degraded in one-step catalytic hydrogenation to produce ethylene glycol with high yield and high selectivity.

To achieve the above objective, the technical scheme of this invention comprises adding reactant polyhydroxy compounds, including cellulose, starch, hemicellulose, glucose, sucrose, fructose, fructan, xylose and soluble xylooligosaccharides, in a sealed high-pressure reactor to undergo catalytic hydrogenation in water. The catalyst is a composite catalyst, comprising catalyst A and catalyst B. The active component of catalyst A comprising a transition metal of Groups 8, 9, or 10 (standard period table, IUPAC system), such as iron, cobalt, nickel, ruthenium, rhodium, palladium, iridium, and platinum, or a mixture thereof. The active component of catalyst B is one or more selected from tungsten oxide, tungsten sulfide, tungsten hydroxide, tungsten chloride, tungsten bronze oxide, tungsten acid, tungstate, metatungstate acid, metatungstate, paratungstate acid, paratungstate, peroxotungstic acid, pertungstate, heteropoly acid containing tungsten. An initial hydrogen pressure in the reactor at room temperature preferably ranges between 1 and 12 MPa. The reaction temperature preferably ranges between 120 and 300° C., and the reaction time being not less than 5 min. More preferably, the reaction temperature ranges between 180 to 250° C., the initial hydrogen pressure inside the reactor is 3 to 7 MPa at room temperature, the reaction time is 30 min to 3 hr.

During the implementation of this process, the weight ratio of the active component of catalyst A to the active component of catalyst B (based on tungsten weight) is between 0.02 and 3000, and preferably between 0.1 and 100.

Conversion of polyhydroxy compounds to ethylene glycol produces intermediate glycol aldehydes, which require catalytic hydrogenation to form ethylene glycol. Therefore, it is necessary for the composite catalyst to contain catalyst A, which is catalytically active for hydrogenation reaction. The active metal component of catalyst A are carried on a carrier chosen from activated carbon, alumina, silica, silicon carbide, zirconia, zinc oxide, titanium dioxide, and/or a mixture thereof. The metal component of the catalyst A accounts for between 0.05 and 50 wt % of the catalyst, and preferably between 1 and 30 wt %. The catalyst A may also be an unsupported skeletal catalyst such as Raney nickel, using the active components as the structural support. The active component of catalyst B in the composite catalyst is chosen from tungsten oxide, tungsten sulfide, tungsten hydroxide, tungsten chloride, tungsten bronze oxide, tungsten acid, tungstate, metatungstate acid, metatungstate, paratungstate acid, paratungstate, peroxotungstic acid, peroxytungstate, heteropoly acid containing tungsten, or a mixture thereof. The tungsten species in the solution play key roles in the catalytic degradation of polyhydroxy compounds during the reaction.

The amount of polyhydroxy compounds and water shall be added when the reactant mixture becomes partially or completely in the form of a liquid solution under the reaction condition. Under this condition, the reactant mixture is stirred to be uniformly heated, avoiding coke formation due to localized hot spots.

Preferably the weight ratio of the polyhydroxy compound to water is between 1:200 and 1:1 and the weight ratio of the polyhydroxy compound to the composite catalyst A+B is between 1:1 and 100:1.

In the following examples, the reactions were carried out in high-pressure reactors. However, other optimally designed reactors cannot be excluded, such as, a fixed bed reactor or a slurry bed reactor, so that the mass transfer and reaction among the polyhydroxy compound, hydrogen, and catalyst are optimized.

Advantages of the invention are summarized below:
1) Producing ethylene glycol using polyhydroxy compounds, e.g., cellulose, starch, hemicellulose, glucose, sucrose, fructose, fructan, xylose or soluble xylooligosaccharides as the raw material. Compared with the conventional processes that use ethylene as the raw material, it has the advantages of using renewable raw material therefore satisfying the requirement of sustainable development;
2) The carbon, hydrogen, and oxygen atoms in the raw materials are retained in the degradation products of the polyhydroxy compounds to a large degree, which means that the preparation method has a high atom economy;
3) The composite catalyst can be easily prepared and convenient to use. Furthermore, the cost of the catalyst is low. The reaction using such composite catalyst has high ethylene glycol selectivity, giving ethylene glycol at a yield of more than 50%, giving it great prospects for commercialization.

DETAILED DESCRIPTION OF THE EMBODIMENTS

Example 1

Preparation of Ni/AC, Ni/SiO$_2$, Pt/AC, Ru/AC Catalysts

Active carbon carriers were impregnated with aqueous solutions of nickel nitrate, chloroplatinic acid, and ruthenium trichloride, respectively. The samples were dried at 120° C. for 12 hrs and reduced in the presence of hydrogen at 450° C. for one hour to yield: a Ni/AC catalyst having 5 wt % nickel, a Pt/AC catalyst having 0.5 wt % platinum, and a Ru/AC catalyst having 5 wt % ruthenium, respectively.

Following the same steps described above, but substituting active carbon with SiO$_2$, a Ni/SiO$_2$ catalyst having 15 wt % nickel was prepared.

Example 2

Preparation of a Nickel-Tungsten Carbide Catalyst

Referring to the literature Angew. Chem. Int. Ed. 2008, 47, 8510-8513, a mixed solution of ammonium metatungstate and nickel nitrate with a W/Ni weight ratio of 15:1 was prepared and the concentration of ammonium metatungstate was 0.4 g/mL. An active carbon carrier was impregnated with the solution, dried in an oven at 120° C. for 12 hrs. One gram of sample thus obtained was carburized in H$_2$ flow (60 ml/min) with a three-stage heating ramp: from room temperature to 400° C. in 1 hour, and then to 700° C. at 1° C./min and holding at this temperature for 1 h. Finally a N$_1$—W$_2$C/AC catalyst having 2 wt % nickel and 30 wt % tungsten was obtained, expressed as N$_1$—W$_2$C/AC (2 wt % Ni-30 wt % W$_2$C).

Example 3

Catalytic Degradation of Polyhydroxy Compounds 1 g polyhydroxy compound, 0.3 g catalyst A, 0.03 g catalyst B and 100 mL of water were added to a 200 mL reactor. The reactor was filled with hydrogen and vented three times to remove air. Subsequently, hydrogen pressure in the reactor was increased to 5 MPa, and then the temperature therein was increased to 240° C. After reacting thirty minutes, the mixture in the reactor was cooled to room temperature and centrifugated to obtain a supernatant. The supernatant was analyzed using high performance liquid chromatography (HPLC) with a calcium ion-exchange column and detected using a refractive index detector. Only the yields of ethylene glycol, propylene glycol, and hexitols (including sorbitol and mannitol) were calculated. The yields of other liquid products, such as erythritol, ethanol, other unknown compounds, and gas products, such as $CO_2$, $CH_4$, $C_2H_6$, etc., were not calculated.

Example 4

Under the reaction conditions described in Example 3, cellulose was degraded in the presence of various composite catalysts. A variety of metals were used in catalyst A while catalyst B was phosphotungstic acid. The results for cellulose conversion using the various composite catalysts described above are shown in Table 1.

TABLE 1

Conversion of cellulose to ethylene glycol in the presence of various catalysts

| Catalyst | Yield of ethylene glycol % | Yield of propylene glycol % | Yield of hexitols % | Other products % |
|---|---|---|---|---|
| Ni/AC + phosphotungstic acid | 56 | 3 | 5 | 36 |
| Pt/AC + phosphotungstic acid | 48 | 3 | 5 | 54 |
| Ni/AC (5% Ni) | 8 | 2 | 48 | 42 |
| Pt/AC (0.5% Pt) | 5 |  | 45 | 50 |
| phosphotungstic acid | 0 | 0 | 0 | 100 |
| Ru/AC + phosphotungstic acid | 60 | 4 | 15 | 21 |
| Ru/AC (5% Ru) | 6 | 0 | 10 | 84 |
| Ni/SiO$_2$ + phosphotungstic acid | 53 | 5 | 8 | 34 |
| Ni/SiO$_2$ (15 wt % Ni) | 5 | 2 | 44 | 49 |
| Ni/Al$_2$O$_3$+ phosphotungstic acid | 33 | 6 | 6 | 55 |
| Ir/TiO$_2$+ phosphotungstic acid | 38 | 7 | 7 | 48 |
| Raney Ni + phosphotungstic acid | 52 | 10 | 7 | 31 |

As shown in Table 1, using various composite catalysts of the invention, cellulose was converted to ethylene glycol in high yield. The yield of ethylene glycol reached 56% using Ni/AC and phosphotungstic acid as a composite catalyst.

Example 5

Under the reaction conditions as described in Example 3, except that catalyst A was Ru/AC, catalyst B was phosphotungstic acid, the results for catalytic conversion of various polyhydroxy compounds are shown in Table 2.

TABLE 2

Conversion of various polyhydroxy compounds in the presence of Ru/AC and phosphotungstic acid as the composite catalyst

| polyhydroxy compound | Yield of ethylene glycol % | Yield of propylene glycol % | Yield of hexitols % | Other products % |
| --- | --- | --- | --- | --- |
| cellulose | 60 | 4 | 15 | 21 |
| starch | 68 | 6 | 10 | 16 |
| hemicellulose | 30 | 24 | 4 | 42 |
| sucrose | 32 | 20 | 15 | 33 |
| glucose | 45 | 5 | 20 | 30 |
| xylose | 30 | 22 | — | 48 |
| soluble xylooligosaccharides | 32 | 23 | — | 45 |
| fructose | 18 | 25 | 25 | 32 |
| inulin | 25 | 28 | 17 | 30 |

As shown in Table 2, various polyhydroxy compounds can be converted into ethylene glycol and propylene glycol in high yields in the catalytic reaction of the present invention.

Example 6

Under the same reaction conditions as in Example 3, except that catalyst A is Ir/AC or Ni/AC while catalyst B is a tungsten containing compound, the results for cellulose conversion in the presence of composite catalysts are shown in Table 3.

TABLE 3

Conversion of cellulose to ethylene glycol in the presence of various catalysts

| Catalyst | Yield of ethylene glycol % | Yield of propylene glycol % | Yield of hexitols % | Other products % |
| --- | --- | --- | --- | --- |
| Ir/AC + $WO_3$ | 45 | 6 | 10 | 39 |
| Ir/AC + $WO_2$ | 48 | 8 | 8 | 36 |
| Ir/AC + phosphotungstic acid ($H_3[P(W_3O_{10})_4] \cdot xH_2O$) | 55 | 4 | 12 | 29 |
| Ir/AC + tungsten acid ($H_2WO_4$) | 50 | 6 | 14 | 30 |
| Ir/AC + silicotungstic acid ($H_4[W_{12}SiO_{40}]$) | 35 | 4 | 30 | 31 |
| Ir/AC + sodium tungstate ($Na_2WO_4$) | 25 | 15 | 16 | 44 |
| Ni/AC + ammonium metatungstate | 59 | 2 | 12 | 27 |

As shown in Table 3, using various composite catalysts of the invention, cellulose can be converted into ethylene glycol in high yield using the catalytic reaction of the present invention.

Example 7

Comparison Between Two Groups of Experiments

In the first group of experiments, the composite catalyst contained Raney nickel as catalyst A, phosphotungstic acid as catalyst B, and active carbon (AC) as the promoter for the degradation of polyhydroxy compounds, while AC is 30 wt % of the total weight of the catalyst. In the second group of experiments, the composite catalyst contained Raney nickel as catalyst A and phosphotungstic acid as catalyst B. The reaction conditions were the same as described in Example 3. The results for catalytic conversion of polyhydroxy compounds are shown in Table 4.

TABLE 4

Results for experiments to compare catalysts

| Group | polyhydroxy compound | Yield of ethylene glycol % | Yield of propylene glycol % | Yield of hexitols % | Other products % |
| --- | --- | --- | --- | --- | --- |
| 1 | starch | 58 | 6 | 10 | 26 |
| 2 | starch | 52 | 3 | 8 | 37 |
| 1 | inulin | 28 | 35 | 16 | 21 |
| 2 | inulin | 22 | 25 | 10 | 43 |

As shown in Table 4, using active carbon as promoter in the catalyst can further improve the yield of polyols, such as ethylene glycol and propylene glycol.

Example 8

Under the same reaction conditions as described in Example 3, expect that catalyst A was Ir/AC or Ni/Ac while catalyst B was a tungsten containing compound. The results for catalytic conversion of starch in the presence of different composite catalysts are shown in Table 5.

TABLE 5

Conversion of starch to ethylene glycol in the presence of various catalysts

| Catalyst | Yield of ethylene glycol % | Yield of propylene glycol % | Yield of hexitols % | Other products % |
| --- | --- | --- | --- | --- |
| Ir/AC + tungsten sulfide | 48 | 4 | 5 | 43 |
| Ir/AC + metatungstate acid | 43 | 9 | 11 | 37 |
| Ir/AC + paratungstate acid | 51 | 2 | 12 | 35 |
| Ir/AC + peroxotungstic acid | 56 | 6 | 9 | 29 |
| Ni/AC + tungsten bronze oxide | 60 | 7 | 8 | 25 |

As shown in Table 5, using various composite catalysts of the present invention, starch can be converted into ethylene glycol in high yield.

Example 9

Table 6 compares the results for conversion of cellulose or starch using preferred catalysts in the present invention with data in the published patents and literature, including China Pat. Appl. No. CN200510008652.0 "A method for producing diols and polyols with sorbitol" and "Direct catalytic conversion of cellulose into ethylene glycol using nickel-promoted tungsten carbide catalysts", Angew. Chem. Int. Ed. 2008, 47, 8510-8513.

TABLE 6

Comparison of results obtained in this invention and published patent and literatures

| Catalyst | Material | Yield of ethylene glycol % |
| --- | --- | --- |
| Ru/AC + phosphotungstic acid | cellulose | 60% |
| Ru/AC + phosphotungstic acid | starch | 68% |
| Ni/AC + Ammonium metatungstate | cellulose | 59% |

TABLE 6-continued

Comparison of results obtained in this invention and published patent and literatures

| Catalyst | Material | Yield of ethylene glycol % |
|---|---|---|
| Ni—$W_2C$/AC Angew. Chem. Int. Ed. 2008, 47, 8510-8513 | cellulose | 61% |
| Ni/Ru (Method disclosed in CN200510008652.0) | Starch was hydrolyzed with an enzyme to yield glucose which was hydrotreated to yield sorbitol | 15% |

As shown in the table, the yield of ethylene glycol following the method of the present invention is obviously higher than reported in CN200510008652.0. Compared with the reported results in Angew. Chem. Int. Ed. 2008, 47, 8510-8513, the yields of ethylene glycol are similar. However, the catalyst preparation in this invention is carried out under milder conditions and the preparation is easier to implement (as demonstrated in the example 1 and 2, comparing the preparation methods).

What is claimed is:

1. A method for producing ethylene glycol from a polyhydroxy compound, comprising the steps of:
   a) reacting a polyhydroxy compound in a reaction environment comprising water, hydrogen, and a catalyst system; and
   b) obtaining a product stream comprising ethylene glycol, wherein the catalyst system comprises catalyst A and catalyst B;
   the active component of catalyst A comprises a transition metal selected from the group consisting of elements in Group 8, 9, or 10 of the Periodic Table;
   the active component of catalyst B comprises a compound selected from a group consisting of tungsten oxide, tungsten sulfide, tungsten chloride, tungsten hydroxide, tungsten bronze oxide, tungsten acid, tungstate, metatungstate acid, metatungstate, paratungstate acid, paratungstate, peroxotungstic acid, pertungstate, heteropoly acid containing tungsten, and a mixture thereof.

2. The method of claim 1, wherein the reaction environment has an initial hydrogen pressure between 1 and 12 MPa at room temperature.

3. The method of claim 1, wherein the reaction temperature is above 120° C.

4. The method of claim 1, wherein the reaction temperature is between 180 and 250° C.

5. The method of claim 1, wherein catalyst A is a supported catalyst wherein the support is selected from the group consisting of activated carbon, alumina, silica, silicon carbide, zirconia, zinc oxide, titanium dioxide, and a mixture thereof.

6. The method of claim 5, wherein the active metal component of the catalyst A accounts for between 0.05 and 50 wt % of the total weight of the catalyst A.

7. The method of claim 1, wherein the catalyst A is a skeletal catalyst.

8. The method of claim 1, wherein the weight ratio of the polyhydroxy compound to water ranges from 1:200 to 1:1.

9. The method of claim 1, wherein the weight ratio of the polyhydroxy compound to a total weight of catalyst A and catalyst B ranges from 1:1 to 100:1.

10. The method of claim 1, wherein a weight ratio of active metal component of catalyst A to the active component of catalyst B, based on tungsten weight ranges from 0.1 to 100.

11. The method of claim 1, wherein the polyhydroxy compound is cellulose, starch, hemicellulose, sucrose, glucose, fructose, fructan, xylose, soluble xylooligosaccharides, or a mixture thereof.

12. The method of claim 1, wherein the polyhydroxy compound is derived from biomass.

13. The method of claim 1, wherein the product stream further comprises propylene glycol.

14. The method of claim 5, wherein the active metal component of the catalyst A accounts for between 1 and 30 wt % of the total weight of the catalyst A.

15. The method of claim 7, wherein the catalyst A is Raney nickel.

16. The method of claim 1, wherein catalyst B is an unsupported catalyst.

17. The method of claim 1, wherein the reaction is carried out in batch mode or in continuous mode.

18. The method of claim 1, wherein the reaction is carried out in a flow reactor chosen from a fixed bed reactor and a slurry reactor.

19. The method of claim 1, wherein the active component of catalyst A comprises a transition metal chosen from iron, cobalt, nickel, ruthenium, rhodium, palladium, iridium, and platinum, and a mixture thereof.

20. The method of claim 1, wherein the active component of catalyst A is nickel.

21. The method of claim 1, wherein a weight ratio of the active component of catalyst A to the active component of catalyst B, based on tungsten weight ranges from 0.02 and 3000.

* * * * *